(12) United States Patent
Sun

(10) Patent No.: US 8,105,549 B2
(45) Date of Patent: Jan. 31, 2012

(54) SAMPLE COLLECTION DEVICE

(75) Inventor: Ming Sun, Cherry Hill, NJ (US)

(73) Assignee: Sun Biomedical Laboratories, Inc (AU)

( * ) Notice: Subject to any disclaimer, the term of this patent is extended or adjusted under 35 U.S.C. 154(b) by 692 days.

(21) Appl. No.: 12/313,347

(22) Filed: Nov. 19, 2008

(65) Prior Publication Data

US 2010/0122587 A1 May 20, 2010

(51) Int. Cl.
*G01N 31/00* (2006.01)
*G01N 33/50* (2006.01)

(52) U.S. Cl. ........................................ 422/417; 422/402

(58) Field of Classification Search .................. 422/417, 422/402, 401, 405, 408, 412, 419–420, 430, 422/68.1, 82.05, 501, 507, 547, 549, 559, 422/561–562, 939, 946–947, FOR. 101, FOR. 103, 422/FOR. 108, FOR. 110, FOR. 112; 73/864, 73/864.72, 864.91
See application file for complete search history.

(56) References Cited

U.S. PATENT DOCUMENTS

| | | | |
|---|---|---|---|
| 4,014,322 A | 3/1977 | Shah | |
| 4,209,488 A | 6/1980 | Breno | |
| 4,387,725 A | 6/1983 | Mull | |
| 5,179,959 A * | 1/1993 | Fishman et al. | 600/556 |
| 5,393,496 A | 2/1995 | Seymour | |
| 6,372,516 B1 | 4/2002 | Sun | |
| 6,740,293 B1 | 5/2004 | Deng | |
| 7,029,627 B2 | 4/2006 | Alley | |
| 7,282,181 B2 | 10/2007 | Hudak et al. | |
| 7,300,627 B1 | 11/2007 | Sun | |
| 8,003,060 B2 * | 8/2011 | Cracauer et al. | 422/430 X |
| 2006/0018800 A1 | 1/2006 | Slowey et al. | |

* cited by examiner

*Primary Examiner* — Thomas P Noland
(74) *Attorney, Agent, or Firm* — St. Onge Steward Johnston & Reens LLC

(57) ABSTRACT

A test sample collection device includes a generally elongated sample collection section for collecting and holding a test sample, a handle member having a top half, a bottom half, a test strip located between the top and bottom halves, and an opening formed by the top and bottom halves, and a cap. Prong members fit within the opening of the handle member for releasably connecting the sample collecting section to the handle member. The cap is releasably mounted on the sample collecting section and covers the sample collecting section. Flexible extension members on the cap are used to release the sample collecting section from the handle member. The collecting section includes a plurality of fins and slots for assisting in collecting the test sample. The device also includes windows for magnified viewing of test results and for indicating whether a sufficient amount of the sample has been collected.

7 Claims, 5 Drawing Sheets

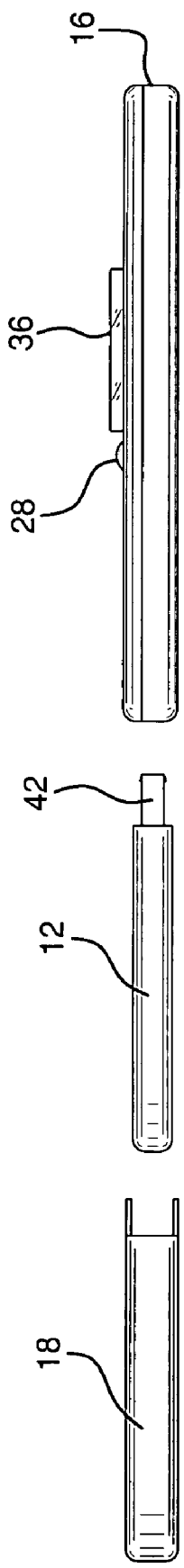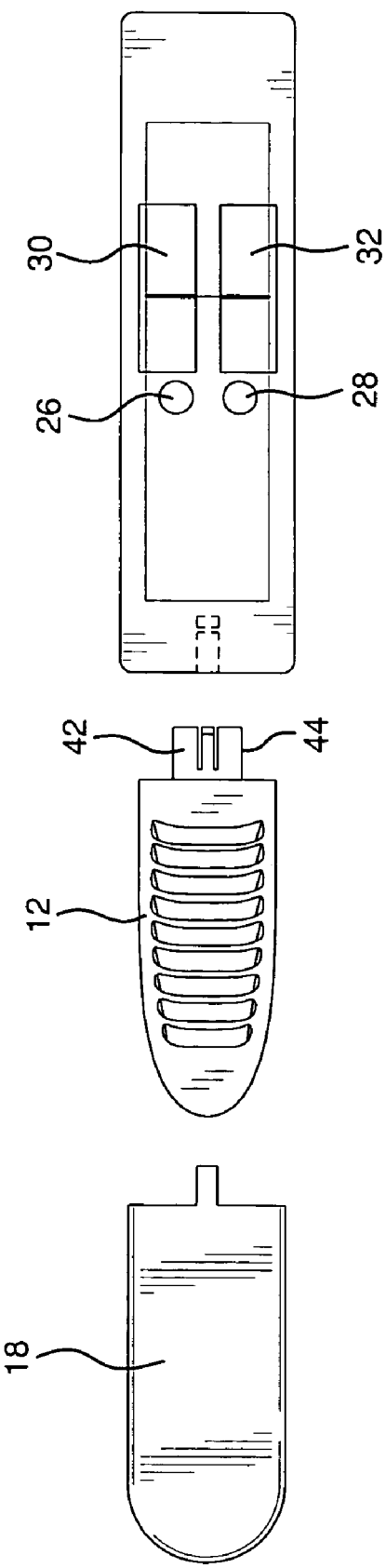
FIG. 6
FIG. 7

SAMPLE COLLECTION DEVICE

BACKGROUND OF THE INVENTION

The present invention is directed toward a test sample collection device for an on site test of saliva or other body fluids and more particularly, toward a device that allows for convenient, accurate and simple collection of the sample.

There are many methods that allow for a test sample to be collected in order to analyze the sample. For example, Applicant's prior patent, U.S. Pat. No. 6,372,516 uses an absorbent pad to collect a sample where the pad comes into contact with a test strip from which a reaction, if any, can be seen. Also, Applicant's prior patent, U.S. Pat. No. 7,300,627 uses a spoon-like device to collect a sample.

Another method for collecting fluid samples currently being used and available through Avitar includes a foam head attached to an elongated handle. Attached to the handle is a hood that is movable along the handle. The foam head is placed into a person's mouth so that fluid enters the foam. The hood is slid forward, over the foam head. The hood is squeezed so that fluid contained therein is expelled into a sample well for testing. This device, however, appears to require a great deal of manipulation and handling of the test device by the person taking the test and the person conducting the test.

Also, further testing of a sample may be required. Taking a second test sample may not be desired or feasible. The methods and devices discussed above may allow for multiple tests being conducted at the same time. However, none of these tests allows for preserving the test sample and allowing that sample to be further tested or analyzed. Furthermore, none of the tests discussed above provides an indicator for sample transfer or a magnified view of the test for easy viewing of test results.

Therefore, a need exists for a test sample collection device that is simple to use, provides accurate results in a quick and consistent manner, and allows the test sample to be analyzed further.

SUMMARY OF THE INVENTION

The present invention is designed to overcome the deficiencies of the prior art discussed above. It is an object of the present invention to provide a test sample collection device that allows for quick and accurate collection of a test sample.

It is another object of the present invention to provide a test sample collection device that is simple to use.

It is a further object of the present invention to provide a test sample collection device that allows for removing the test sample from the test device and preserving the test sample for further analysis.

It is yet another object of the present invention to provide a test sample collection device that provides a test result that is east to read.

In accordance with the illustrative embodiments demonstrating features and advantages of the present invention, there is provided a test sample collection device that includes a generally elongated sample collection section for collecting and holding a test sample, a handle member having a top half, a bottom half, a test strip located between the top and bottom halves, and an opening formed by the top and bottom halves, and a cap. Means fit within the opening of the handle member for releasably connecting the sample collecting section to the handle member. The cap is releasably mounted on the sample collecting section and covers the sample collecting section. Tabs on the cap fit within the opening of the handle member for releasing the sample collecting section from the handle member. The collecting section includes a plurality of fins for assisting in collecting the test sample.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings one form that is presently preferred; it being understood that the invention is not intended to be limited to the precise arrangements and instrumentalities shown.

FIG. 6 is an exploded side elevational view of the device of the present invention;

FIG. 7 is an exploded top plan view of the device of the present invention.

DETAILED DESCRIPTION OF THE EMBODIMENT

Figure 1:
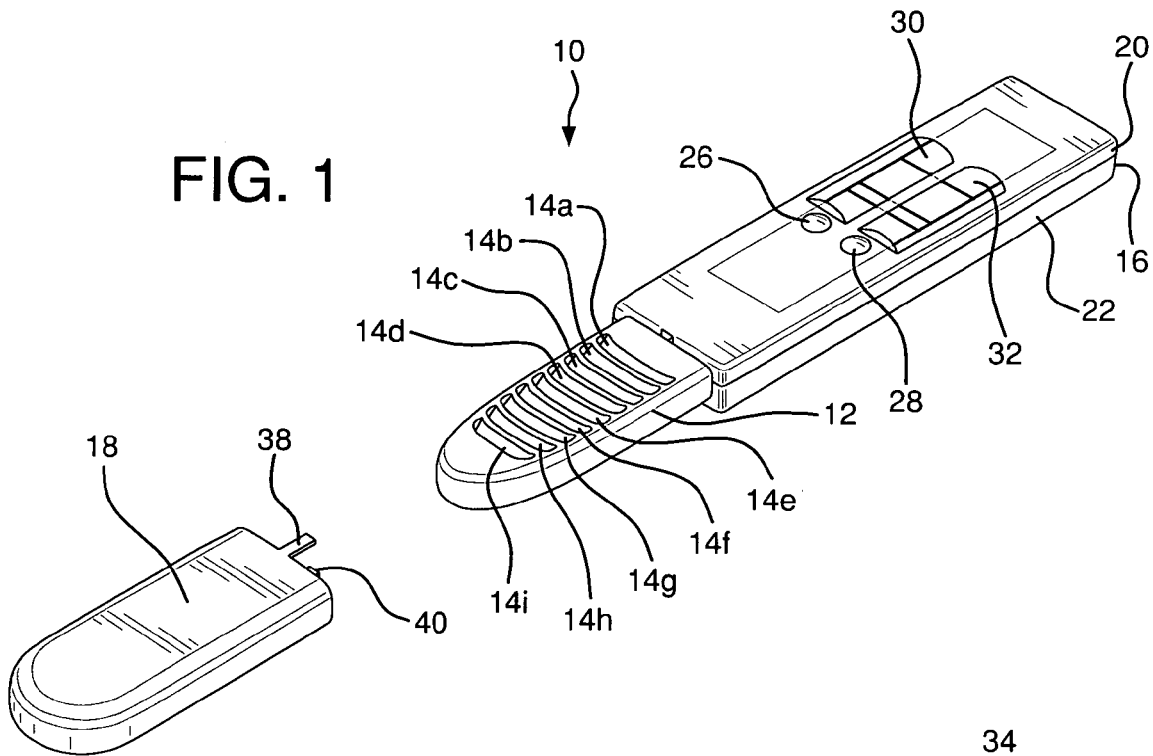
FIG. 1 is a front perspective view of the sample collection device of the present invention.

Referring now to the drawings in detail wherein like reference numerals have been used throughout the various figures to designate like elements, there is shown in FIG. 1 a test sample collection device constructed in accordance with the principles of the present invention and designed generally as 10.

Figure 2:
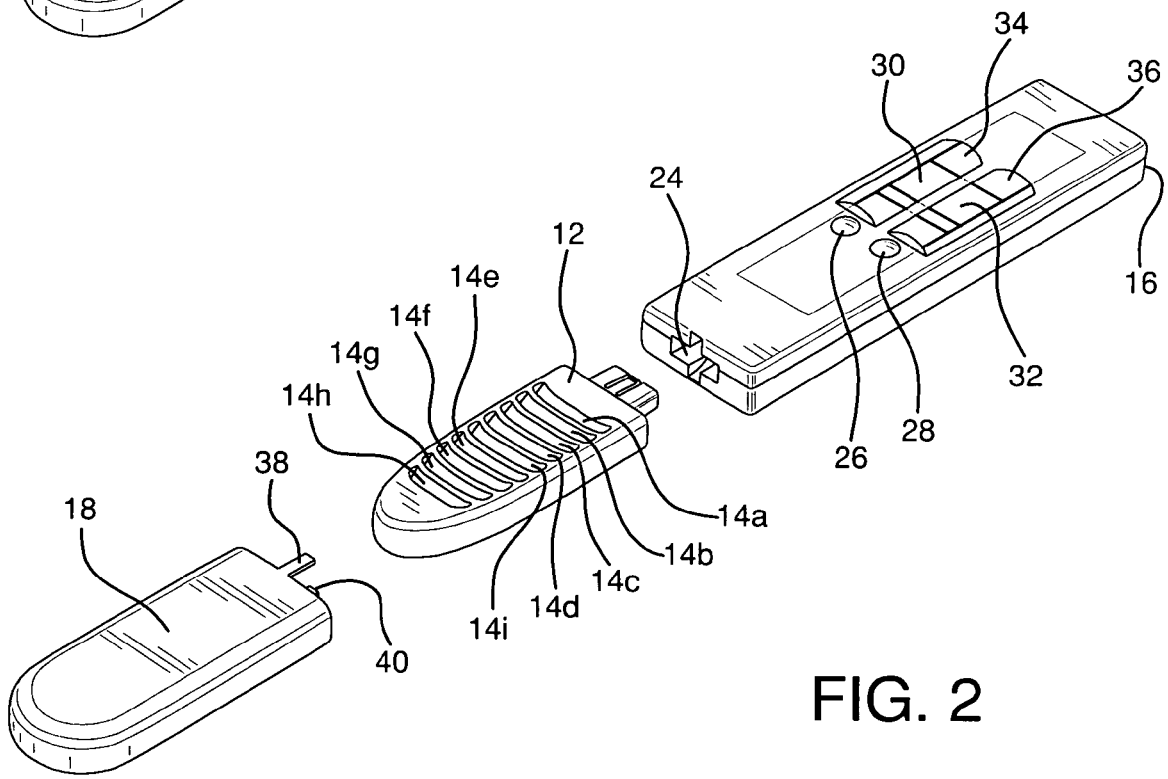
FIG. 2 is an exploded perspective view of the device of the present invention.

The test sample collection device of the present invention essentially includes a generally elongated sample collecting ridged section 12 having a plurality of fins 14a-14j for assisting in collecting and holding a liquid test sample as will be discussed in greater detail below. The device also includes a handle member 16 housing a test strip and a channel member providing means for transferring the test sample to the test strip. A generally elongated cap 18 is releasably mounted on the ridged section 12 and covers the channel member and the ridged section 12. The sample collecting section 12 is releasably connected to the handle member 16 as will be discussed in greater detail below. (See FIG. 2.)

Figure 3:
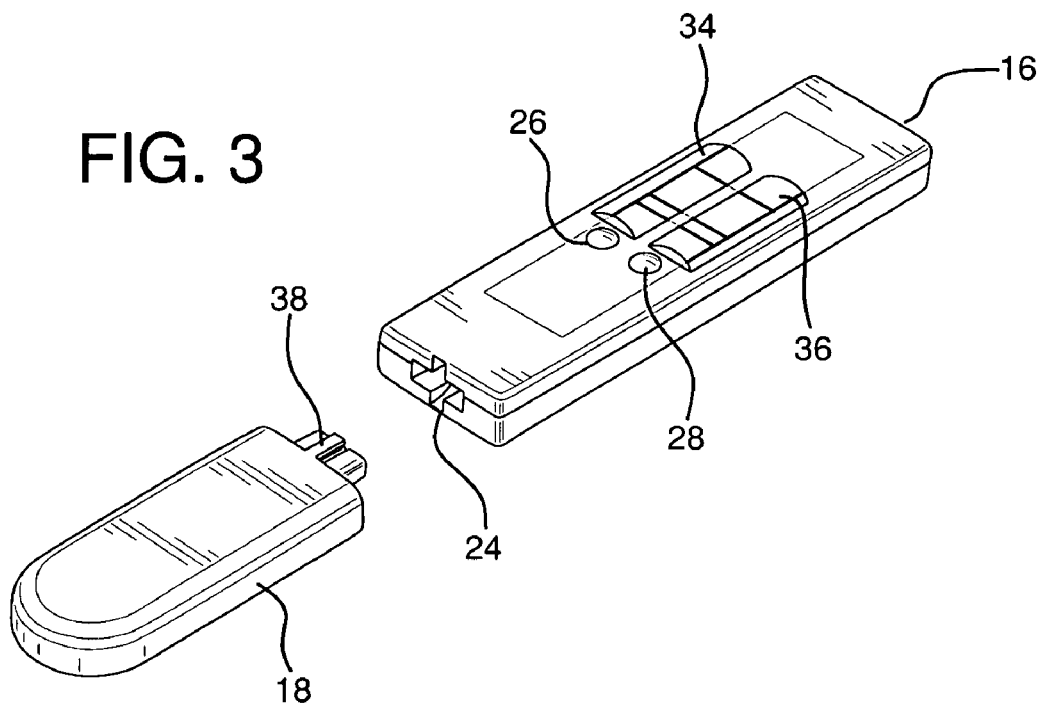
FIG. 3 illustrates the cap and sample collecting section of the present invention detached from the rest of the device.

The handle member 16 includes a top half 20 and a bottom half 22 with at least one test strip located therebetween. The top and bottom halves 20 and 22, respectively, fit together in a manner typically known in the art, thereby forming a housing with a generally cross-shaped opening 24 formed at one end. (See FIG. 3.) For example, pins may be located along the inside perimeter of the top half of the housing where each pin fits in a respective hole formed along the periphery of the interior of the bottom half of the housing. The top half of the housing may be made from an optically clear grade plastic material such as polycarbonate or ABS, for example. A first set of indicator windows 26 and 28 is located in the top half 20 of the housing 16 so that sample transfer may be confirmed.

Figure 4:
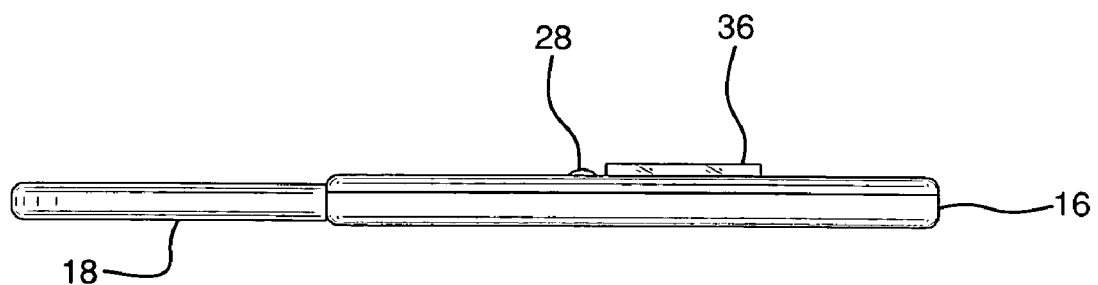
FIG. 4 is a side elevational view of the device of the present invention.
Figure 5:
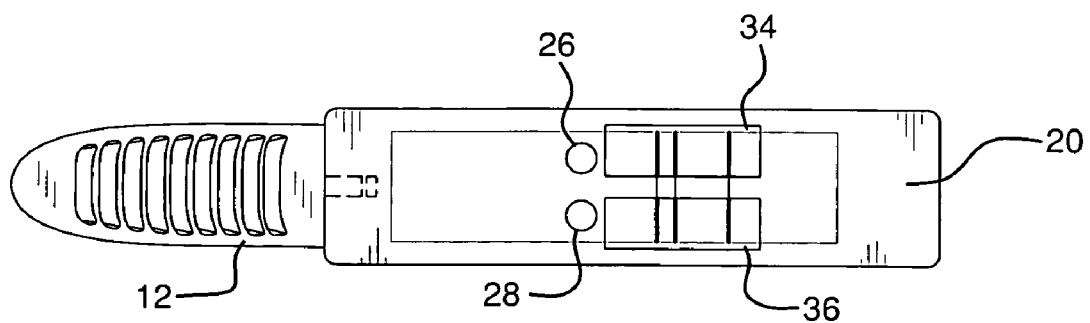
FIG. 5 is a top plan view of the device of the present invention.

Another set of larger windows 30 and 32 are also located in the top half 20 of the housing 16 so that the test reaction may be seen therethrough. Each of the larger windows 30 and 32 may include a convex/convexo-concave plastic cover 34 and 36, respectively, so that the test reactions are magnified and could be read easily. (See FIGS. 4 and 5.)

The test strip may be an immunoassay test strip of the type described in Applicant's prior U.S. Pat. No. 6,372,516. However, almost any type of test strip may be used. The test strip may be used to analyze any type of substance as well. For example, the test device may be used to test for the presence of particular drugs in saliva. Also, one or more test strips may be used in a single device. While two test strips have been shown in the figures it should be realized that this is by way of example only and that the device may include a single test or more than two tests.

Figure 11:
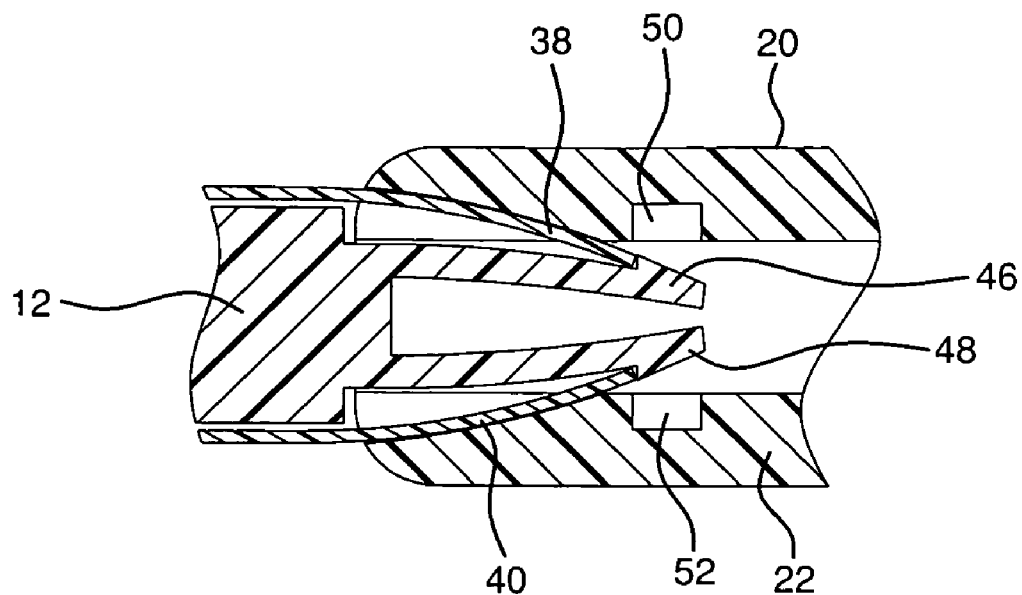

The cap 18 includes generally flexible outwardly extending extension or tab members 38 and 40 that bend slightly and fit snugly within the opening 24 of the housing 16. (See FIG. 11.) The transferring means of the channel member includes an elongated passageway connecting the ridged section 12 with the housing 16. The passageway acts as a conduit for the test sample. That is, the test sample flows from the ridged section 12 to the test strip. The manner for transferring the test sample from the sample collecting section to the test strip is similar to the mechanism described in Applicant's prior U.S. Pat. No. 7,300,627. The housing may also include means for illuminating the test device. For example, the interior of the housing may include a structure that is angularly cut to conduct and reflect the illuminating light in order to facilitate night vision and viewing of the test results. The illuminating means may also be used to detect the results from a fluorescent labeled test marker.

Figure 8:
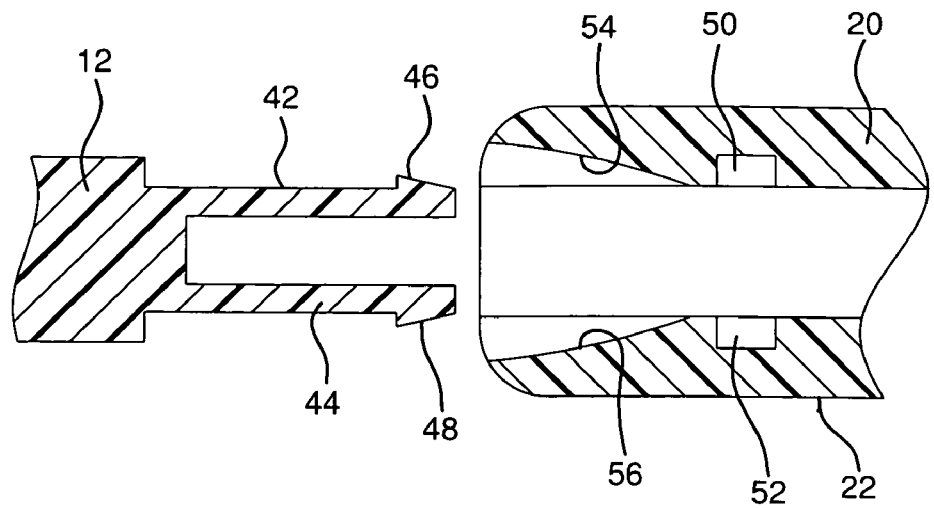
FIGS. 8-12 illustrate the assembly and removal of the sample collecting section and cap of the device of the present invention.
Figure 9:
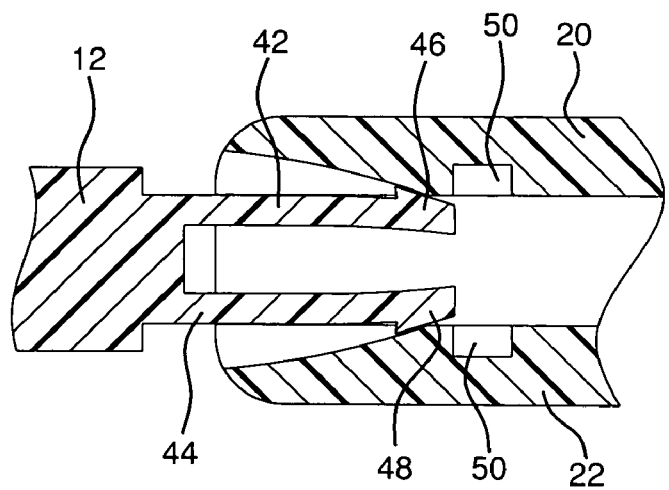
Figure 10:
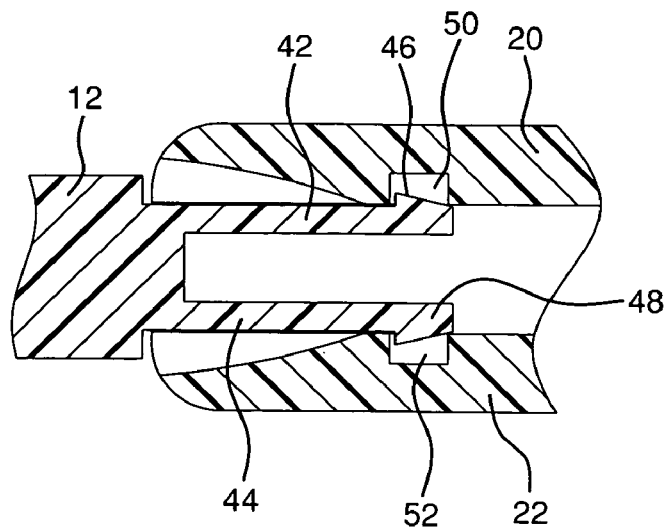

As shown most clearly in FIGS. 8-10, the sample collection section 12 is removably attached to the housing 16 through two outwardly extending prong members 42 and 44 that are inserted into the opening 24 of the handle member 16. (FIGS. 8 and 9.) The barbed tips 46 and 48 of the prong members 42 and 44, respectively, fit within respective apertures 50 and 52 formed within the housing 16 and are releasably secured therein. (See FIG. 10.)

In order to use the device of the present invention, the cap 18, which is initially loosely resting on the sample collection section 12 is removed from the device by simply sliding it off. The sample collection section 12 is then used to collect the test sample. This may involve placing the ridged section into a person's mouth so that saliva is scraped from the tongue or other portions of the mouth. The sample flows through the sample collection section and onto the test strip in a quick and controlled manner without over or under saturation of the test strip. The sample reaches the reaction zone of the test strip via capillary action in the known manner. Any reactions may be viewed through the windows 30 and 32.

Figure 12:
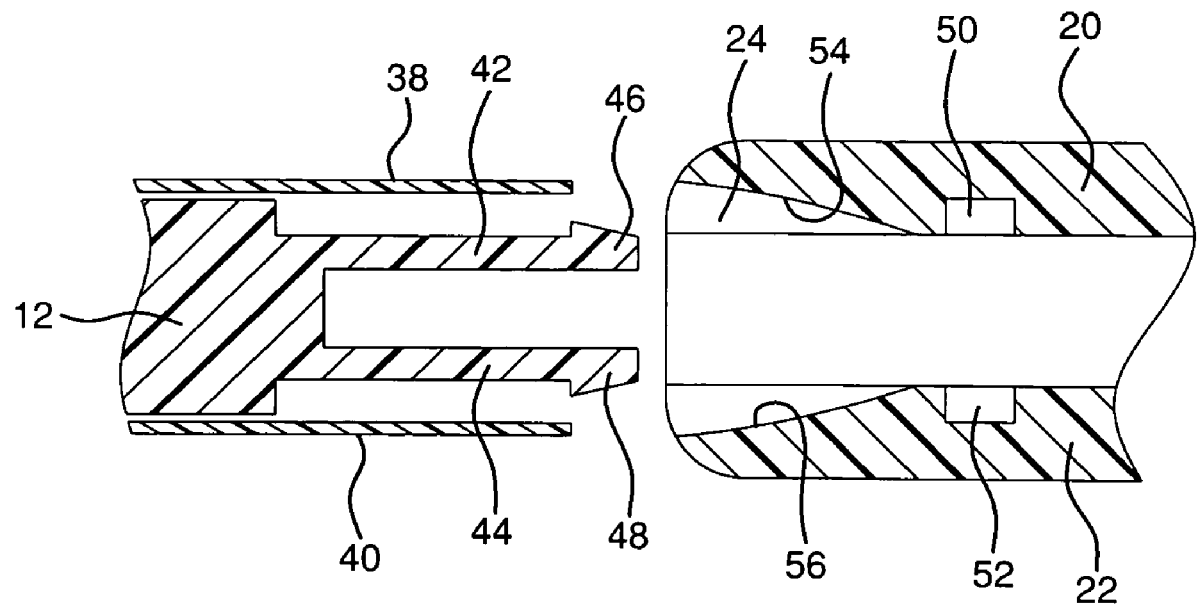

If further testing is required, the cap 18 may be removed along with the sample collecting section 12 of the device from housing 16 so that the sample may be sent away for further analysis or for the initial results to be confirmed. In order to remove the sample collection section 12 from the housing 16, the cap 18 is placed over the section 12 and moved inwardly toward the housing 16. As the cap is moved inwardly, the tabs or extension members 38 and 40 enter the opening 24 and engage the curved walls 54 and 56, respectively. (See FIGS. 11 and 12.) Upon further movement, the tabs 38 and 40 eventually engage the prong members 42 and 44 and cause the tips 46 and 48 of the prongs 42 and 44, respectively, to be released from the apertures 50 and 52 so that the cap 18, with the ridged section 12 therein, is released from the housing 16. (See FIGS. 11 and 12.) The covered sample collection section 12 can then be sent to a lab or the like for further analysis.

The device may be made from polyethylene, overmolded TPE for the fins, or similar material having some flexibility. The fins may be formed in a variety of arrangements. For example, the fins may be arranged in a zigzag manner. The fins may also be located on one or both sides of the section 12. Also, the ridged section may be angled or inclined slightly with a plurality of slots located therebetween at an angle from 90-30 degrees. This structure aids in stimulating and facilitating saliva collection. The device may also include a moisture indicator to indicate whether a sufficient amount of test sample has been collected.

The present invention may be embodied in other specific forms without departing from the spirit or essential attributes thereof and accordingly, reference should be made to the appended claims rather than to the foregoing specification as indicating the scope of the invention.

I claim:

1. A test sample collection device comprising:
   a generally elongated sample collection section for collecting and holding a test sample, the sample collecting section having a plurality of fins;
   a handle member having a top half, a bottom half, a test strip located between said top and bottom halves, and an opening formed by said top and bottom halves;
   means for releasably connecting said sample collecting section to said handle member;
   a generally elongated cap releasably mounted on said sample collecting section and covering said sample collecting section; and
   means associated with said cap for releasing said sample collecting section from said handle member.

2. The test sample collection device of claim 1 wherein said means for releasably connecting said sample collecting section to said handle member includes outwardly extending prong members on said sample collection device that releasably fit within said opening of said handle member.

3. The test sample collection device of claim 1 wherein said cap includes tabs extending therefrom that interact with said prong members to release said prong members from said handle.

4. The test sample collection device of claim 1 further including a set of convex windows for viewing any test reactions.

5. The test sample collection device of claim 4 wherein at least one of said windows includes means for amplifying the test reactions.

6. The test sample collection device of claim 1 wherein said plurality of fins includes a plurality of slots located therebetween, said slots being arranged at an angle from 90 and 30 degrees.

7. The test sample collection device of claim 1 further including means for indicating whether a sufficient amount of sample has been collected.

* * * * *